(12) United States Patent
Garolla

(10) Patent No.: US 11,717,224 B2
(45) Date of Patent: Aug. 8, 2023

(54) PATIENT SUPPORT DEVICE, SUCH AS A PATIENT BED, TABLE OR CHAIR, FOR USE WITH MAGNETIC RESONANCE IMAGING APPARATUSES

(71) Applicant: Esaote S.p.A., Genoa (IT)

(72) Inventor: Roberto Garolla, Genoa (IT)

(73) Assignee: ESAOTE S.P.A., Genoa (IT)

( * ) Notice: Subject to any disclaimer, the term of this patent is extended or adjusted under 35 U.S.C. 154(b) by 261 days.

(21) Appl. No.: 17/071,119

(22) Filed: Oct. 15, 2020

(65) Prior Publication Data
US 2021/0113112 A1 Apr. 22, 2021

(30) Foreign Application Priority Data

Oct. 16, 2019 (EP) ..................................... 19203595

(51) Int. Cl.
| | |
|---|---|
| *A61B 17/225* | (2006.01) |
| *A61B 5/00* | (2006.01) |
| *A61B 5/055* | (2006.01) |
| *A61G 13/12* | (2006.01) |
| *A61B 6/04* | (2006.01) |
| *G01R 33/34* | (2006.01) |

(52) U.S. Cl.
CPC .......... *A61B 17/2255* (2013.01); *A61B 5/704* (2013.01); *A61B 5/0033* (2013.01); *A61B 5/055* (2013.01); *A61B 6/04* (2013.01); *A61B 6/0407* (2013.01); *A61B 6/0421* (2013.01); *A61G 13/12* (2013.01); *G01R 33/34007* (2013.01)

(58) Field of Classification Search
CPC ..... A61B 17/2255; A61B 5/704; A61B 5/055; G01R 33/34007
See application file for complete search history.

(56) References Cited

U.S. PATENT DOCUMENTS

| | | | | | |
|---|---|---|---|---|---|
| 5,197,474 | A | * | 3/1993 | Englund | .......... G01R 33/56383 324/318 |
| 5,363,845 | A | * | 11/1994 | Chowdhury | .......... G01R 33/365 324/318 |
| 6,023,166 | A | * | 2/2000 | Eydelman | .......... G01R 33/3415 324/318 |

(Continued)

FOREIGN PATENT DOCUMENTS

EP 1732438 B1 5/2017

*Primary Examiner* — Dixomara Vargas
(74) *Attorney, Agent, or Firm* — Buchanan Ingersoll & Rooney PC

(57) ABSTRACT

A patient support device includes a patient support surface having a size to accommodate at least a part of the patient body, the device including at least one receptacle for housing a coil, which at least one receptacle is arranged in an area of the patient supporting surface corresponding to the position of the anatomic region to be imaged, the patient support surface being covered at least partially by one or more cushions covering in combination the entire patient supporting surface or at least a part of it. At least one of the receptacles for coupling to a receiving coil being provided on at least each of one or more than one of the said cushions, the coil once coupled to a corresponding receptacle is connected to a control and processing unit of the MRI apparatus by means of a cable which is external to the said patient support device.

17 Claims, 5 Drawing Sheets

(56) References Cited

U.S. PATENT DOCUMENTS

| | | | | |
|---|---|---|---|---|
| 7,844,318 | B2* | 11/2010 | Rezzonico | A61B 5/055 |
| | | | | 600/410 |
| 2003/0128033 | A1* | 7/2003 | Sinkus | A61B 5/055 |
| | | | | 324/309 |
| 2008/0211498 | A1* | 9/2008 | Dannels | G01R 33/3415 |
| | | | | 324/309 |
| 2009/0306494 | A1* | 12/2009 | Scarth | G01R 33/341 |
| | | | | 378/63 |
| 2010/0102814 | A1* | 4/2010 | Satragno | A61B 5/055 |
| | | | | 324/309 |
| 2010/0135559 | A1* | 6/2010 | Morich | G01T 1/1647 |
| | | | | 382/131 |
| 2010/0315087 | A1* | 12/2010 | Thulborn | G01R 33/485 |
| | | | | 324/318 |
| 2012/0133365 | A1* | 5/2012 | Davis | G01R 33/34084 |
| | | | | 324/318 |
| 2012/0265053 | A1* | 10/2012 | Rohr | A61B 5/055 |
| | | | | 600/415 |
| 2014/0145717 | A1* | 5/2014 | Ozawa | G01R 33/3664 |
| | | | | 324/318 |
| 2014/0213886 | A1* | 7/2014 | Menon | A61B 5/704 |
| | | | | 600/411 |
| 2015/0196255 | A1* | 7/2015 | Rehner | G01R 33/387 |
| | | | | 600/415 |
| 2016/0069975 | A1* | 3/2016 | Rothberg | G01R 33/383 |
| | | | | 324/322 |
| 2016/0238677 | A1* | 8/2016 | Fischer | G01R 33/3415 |
| 2017/0299669 | A1* | 10/2017 | Hesels | G01R 33/30 |
| 2019/0128978 | A1* | 5/2019 | Zink | A61B 5/055 |
| 2019/0154775 | A1* | 5/2019 | Stack | G01R 33/34084 |

* cited by examiner

PATIENT SUPPORT DEVICE, SUCH AS A PATIENT BED, TABLE OR CHAIR, FOR USE WITH MAGNETIC RESONANCE IMAGING APPARATUSES

The invention relates to a patient support device, such as a patient bed, table or chair, for use with Magnetic Resonance imaging apparatuses, wherein said device comprises a patient supporting surface having such a size as to accommodate at least a part, particularly the whole of the patient body.

BACKGROUND OF THE INVENTION

Several different types of Magnetic Resonance imaging apparatuses are known in the art. One of these is a total body scanner apparatus, whose magnet structure can accommodate the whole patient body, or a considerable part thereof, within an imaging volume defined by the magnet structure. The patient is carried into the imaging volume by a positioning device, such as a patient bed or table mounted on a cart. Such type of apparatuses have a number of drawbacks: they have a large size, a heavy weight and a high cost and may easily cause problems during installation, i.e. they have to be installed in facilities of such a size and structural strength as to fit the size and the weight of the apparatus, which involves a further cost increase.

In a second prior art arrangement an apparatus with a smaller magnet is used, and a part of the patient body is only introduced in the imaging volume, means being provided for coupling the patient support device and the magnet. However, since the receiver coil is typically secured in a fixed location within the apparatus, the patient support device requires rather complex handling, to move the anatomic region to be examined into coincidence with such receiver coil, or elements must be provided outside the patient support device, having tilting parts or the like, and in certain cases the patient must be forced to move, which is not desirable especially for patients affected with certain diseases. Eventually, this arrangement does not provide an optimal synergy between the patient support device and the Magnetic Resonance apparatus.

Actual coils for receiving coils for receiving the RF MRI echoes, are further mounted above the patient supporting surface and are shaped in such a way as to at least partially surround the body to be imaged or the part of the body to be imaged. This kind of coils has the drawback that it can be used comfortably only for some anatomical district of the body to be imaged. For example for the anatomical district of the spine such kind of known receiving coils would need very big dimensions and request correspondingly bigger structures of the imaging apparatus which must allow to place inside particularly a cavity of a magnetic resonance apparatus not only the body to be imaged or part of it but also the receiving coil. Normally inside the cavity of the MRI apparatus also a patient supporting device must fit together with the body to be imaged or the part of the body to be imaged and the correspondingly shaped and dimensioned receiving coil.

FIG. 1 shows an MRI apparatus according to the state of the art and comprising a patient support table slidably secured to a pole of a magnet and which support table is provided distributed over its surface with a certain number of coils securing seats each seat being positioned approximatively at the position of an anatomic district to be imaged when the patient is positioned on the supporting table.

The Magnetic Resonance Imaging apparatus according to this example comprises a support element in the form of a vertical wall 1. A magnet structure 2 is overhanging secured to said support element. The magnet structure 2 comprises two opposed pole pieces 102, 202, which are oriented perpendicular to the vertical support wall 1. These pole pieces 102, 202 are at a certain predetermined distance from each other and are connected by a column or wall 302 extending parallel to the vertical support wall 1. A patient support surface 7, essentially formed by a patient table is mounted on the lower pole piece 102 of the magnet structure 2 with its longitudinal axis perpendicular to the axis of the shaft and parallel to the wall 302 of the magnet structure 2. The support surface 7 is supported in such a manner as to be able to slide parallel to its own longitudinal axis, thanks to a combination of guides and slides, motor-driven means being provided to achieve proper positioning of the support plane 7 relative to the magnet structure 2. A plurality of receptacles 12 each for removably locking the base 113 of a receiver coil 3 are provided on the bottom face of the lying patient support surface 7. In the embodiment receptacles 12 are provided in symmetric pairs, with respect to the longitudinal center axis of the support surface 7, and particularly level with the two shoulders, the two elbows, the two wrists, the two knees and the two ankles of the patient, with reference to the lying position of the patient at the center of the support plane 7. The said receptacles are destined to cooperate with a securing socket or foot of coils. These foots or sockets are shaped and configured in such a way as to engage in a releasable manner a corresponding receptacle. The arrangement of coils resulted from an ergonomic analysis associated to the evaluation of anthropometric data, but any other arrangement that is deemed to be useful may be provided. The receptacles of this embodiment have a predetermined position on the patient support table or surface and must be provided and planned already at the very beginning of the configuration and design process of the patient support table. After the construction of the said table the receptacles cannot be anymore modified in relation to their configuration. Their number and their position on the patient support surface or table. AN example of the above described prior art device is disclosed in document EP1732438 of the same applicant.

Obviously, the coils may also have different shapes, depending on the anatomic region for which they are designed. A mattress is provided on the top face of the support surface 7, to increase patient comfort, and the base of each coil has such an axial extension as to allow introduction thereof in its locking receptacle by passing through a through hole formed in the mattress. The holes that are not used during a particular examination may be closed by bearing-like closing members, which may be made from the same material as the mattress or from another material. The base of each coil and each receptacle have complementary means for removably locking the base of the coil, which may be, for instance, a press-fit terminal provided at the lower end of the base and a complementary press-fit recess provided at the bottom of the receptacle. An annular widened portion of the base of each coil is further provided which, when the base is fitted in its receptacle, abuts against the corresponding annular periphery of the receptacle, thereby allowing proper automatic height positioning of each coil relative to the support surface, and allowing the coil to project above the mattress to the required extent.

The present invention has the purpose of obviating the above drawbacks and providing, by simple and inexpensive means a patient support device as described hereinbefore, which is capable of being combined with a relatively small, light and inexpensive apparatus. Patients should be easily placed on the support device, and the positioning of the relevant anatomic region should be fast and safe, with no movement possibly having to be performed by patients, especially when several different anatomic regions have to be examined.

Another object of the present invention relates to providing a patient support device which is functional and low cost allowing at the same time to be very flexible in relation to changing the position of the receptacle at which a receiving coil can be secured and also the configuration of a receptacle for bringing the said receptacle in conformity with different configurations of the securing socket or foot of a coil.

As it will be apparent from the following description modifying the position of a coil and/or the adapting the receptacles to a different configuration of the securing socket is easy, costs less and is also relatively rapid.

The invention achieves the above objects by providing a patient support device such as a patient bed, table or chair, for use with Magnetic Resonance Imaging apparatuses, wherein said device comprises a patient support surface having such a size as to accommodate at least a part of the patient body, particularly the whole of the patient body, the said device comprising at least one receptacle (307) for housing and/or removably coupling a coil (13') adapted to receive signals from anatomic regions upon excitation thereof by the Magnetic Resonance Imaging apparatus, which at least one receptacle (307) is arranged in an area of the patient supporting surface corresponding to the position of the anatomic region to be imaged, the said patient support surface being covered at least partially by one or more cushions covering in combination the entire patient supporting surface or at least a part of it.

According to an embodiment of the present invention, at least one of the said receptacles for coupling to a receiving coil being provided on at least each of one or more than one of the said cushions, the coil once coupled to a corresponding receptacle is connected to a control and processing unit of the MRI apparatus by means of a cable which is external to the said patient support device.

According to an embodiment the cable external to the patient support device is a cable departing from the coil and comprising electrical conductors connected electrically to the coil the said cable ending at its end opposite to the coil with a plug to be inserted in a socket which is provided on the case of the apparatus and from which connectors departs to the processing unit of the MRI apparatus. In this way no electric connection line of the coil to the processing unit of the apparatus has to be proved inside the patient support device and/or inside the cushion/s.

According to an embodiment, each one of the said cushions is physically separated from the other cushions and the position of all or of at least some of the said cushions relatively to the length of the patient support surface can be exchanged among the said at least some cushions so that all or at least some of the said cushions can occupy different alternative positions relatively to the length of the said patient support surface, thereby changing the position of the receptacle for housing or removably coupling a coil provided on a corresponding cushion relatively to the length of the said patient support table and to the anatomy of the patient.

According to an embodiment at least part of the cushions have an extension in the direction perpendicular to the longitudinal axis of the said support device, which extension corresponding essentially to the width of the said patient support surface.

According to an embodiment, the said cushions have an extension in the longitudinal direction of the said patient support device and the said cushions being provided in such a number that the sum of the extensions of the said number of cushions provided is essentially equal to the longitudinal extension of the said patient support surface.

In a further embodiment the extension of the said cushions in the direction parallel to the longitudinal axis of the patient support surface is selected such that the corresponding receptacle for coupling a receiving coil is essentially in a position corresponding to an anatomical district which is diagnostically interesting for being examined by MRI imaging when a patient is positioned on the patient support device.

According to a further embodiment, the extension of the said cushions in the direction parallel to the longitudinal axis of the patient support surface is calculated as a function of the average dimensions of the anatomical structure of a normal adult person and/or of a child.

According to still a further embodiment, cushions are provided which do not show any receptacle for securing a coil, while in combination therewith dedicated coil securing plates which are coils specifically designed cushion or element substituting at least one cushion are provided, these coil securing plates having at least one receptacle for securing at least one coil, the said coil securing plates having the dimensions of a corresponding cushion.

In combination with one or more of the preceding embodiments or variants, a further embodiment provides for a coil having a coil foot designed for engaging a corresponding receptacle, the said coil foot comprising a lower extension destined to engage the receptacle and projecting out of an enlarged base which is destined to adhere to the surface of the coil securing plate when the lower projection is engaged in the receptacle.

AS can be appreciated form the above, differently from the cited prior art the patient support device according to the present invention allows to obtain many advantages such as:

Simplify coils positioning in relation to anatomic districts;

Reduce number of different coils positioning sockets;

Simplify patient table/cushions construction.

In a preferred embodiment which will be described with more detail in the following, the coil supporting cushions have identical dimensions as normal cushions.

Eccentric coil seat coupling with unitary coil socket for several kinds of coils in combination with the cushions extending from side to side of the table allows easy positioning for right and left districts (leg, knee, arm, shoulder) by simply rotating the cushion of 180°.

The special socket construction in combination with controlled deformation behavior of the cushion ensure positioning stability of the coil; enlarged contact surface with the cushion in combination with support also on the hard part of the table.

Furthermore special coil bearing cushions for all coils having central position (head, spine, cervical, mandibular), easily interchangeable can be provided very easily and maintaining costs low.

According to still a further embodiment which features can be provided in any combination with one or more of the previously described combination of features, the said support device is provided in combination with at least one NMR signal receiving coil, the said coil being provided with a socket configured to engage a corresponding receptacle and the said patient support device comprising a patient support surface and a set of cushions dimensioned such that the set of cushions covers, when positioned on the said patient support surface, quite the entire extension of the said surface;

the said set of cushions further comprising at least one first cushion provided with a coil securing receptacle configured to releasable engage the securing socket of a receiving coil;

at least a further cushion having a coil securing receptacle which is modified relatively to the said first cushion in relation to the position of the said receptacle along the said cushion surface and/or in relation to the design or configuration of the said receptacle for being in conformity with a further different socket;

at least a further cushion not showing any receptacle but having different dimensions, particularly a different extension in at least one direction particularly in a direction parallel to the longitudinal axis of the patient support device.

In a variant embodiment, two or more set of cushions are provided each set comprising at least one cushion with a coil securing receptacle, at least one cushion without any receptacle, the said sets of cushions having dimensions in the direction of the longitudinal axis of the patient support device which are determined as a function of the height of samples of patient body having different heights.

According to an example of such variant embodiment, the samples of patient body are selected among the ones in the following list: baby, adolescent, adult, small, medium and tall adult.

As it appears from the above embodiments, the patient support device can be very easily adapted or upgraded to the configuration and design of new or different kinds of receiving coils to be positioned and secured on it. This by simply providing a differently configured cushion having identical or quite identical overall dimensions of the existing cushions and bearing a differently designed and/or configured receptacle and/or a receptacle positioned differently on the extension of the corresponding cushion.

The provision of different sets of cushions allows to adapt the sets to different body sizes. Considering a certain flexibility of positioning a patient on the table, only a reduced number of sets may be necessary which are adapted in relation to mean sizes of the body of a person in relation to age and/or to physical type.

SHORT DESCRIPTION OF THE DRAWINGS

The characteristics of the invention and the advantages derived therefrom will be more apparent from the following detailed description of embodiments shown in the accompanying drawings, in which.

Figure 7:
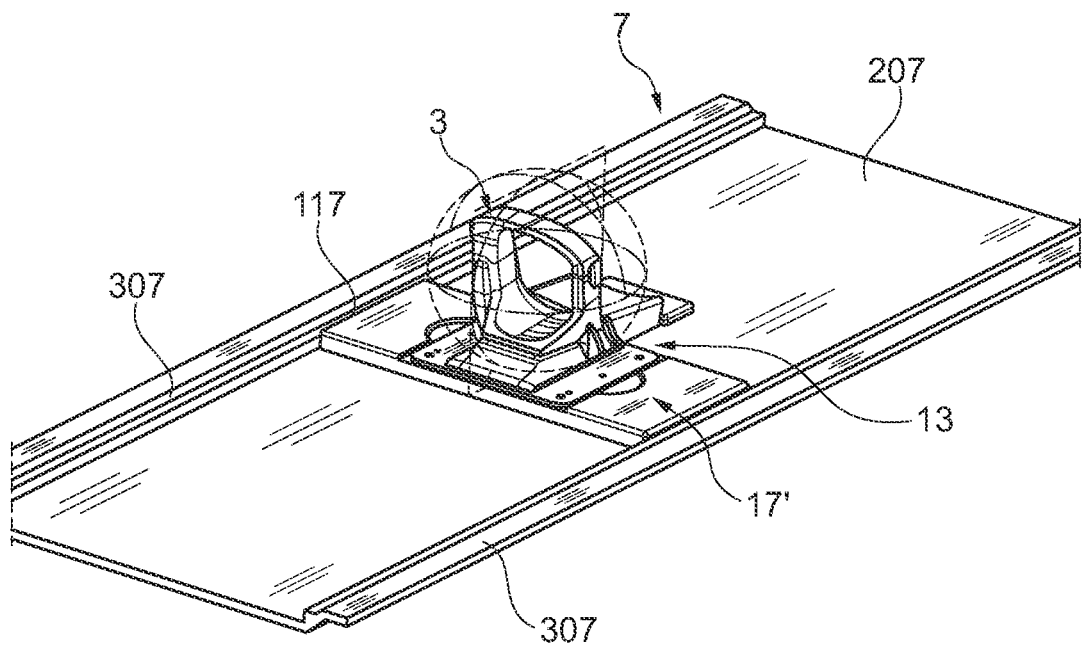
Figure 8:
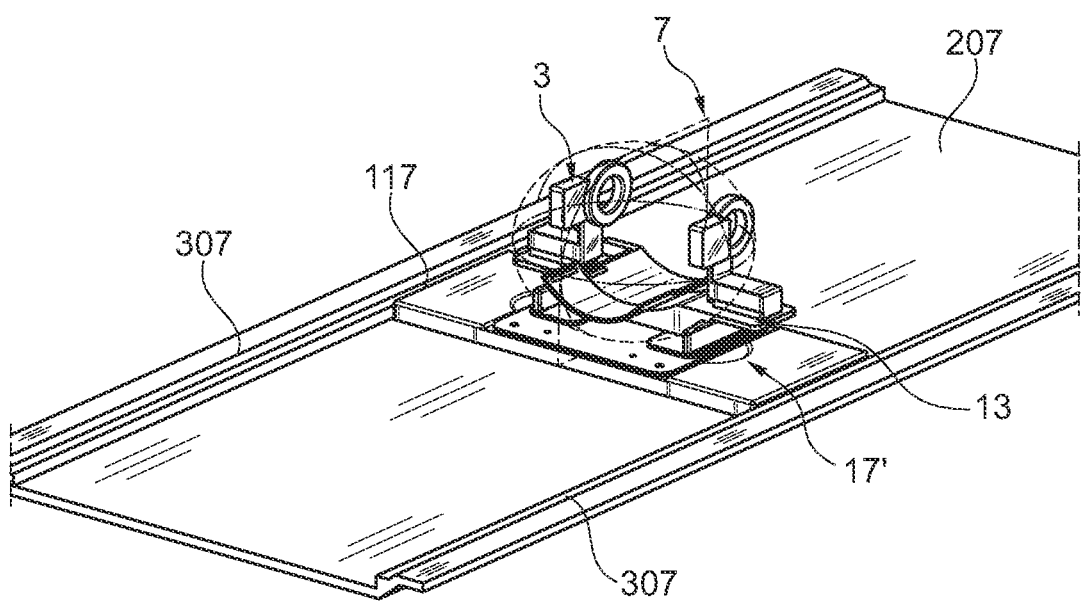

FIGS. 7 and 8 respectively show perspective views of constructive variant embodiments relating to a differently configured coil.

In relation to the embodiments shown in the drawings, the patient support device is described in a specific example in combination of an open C shaped magnet and in this case the table is slidably secured to the magnet structure.

It is worth to notice that this example is in no way limitative and that the teaching of the present invention can be applied to any kind of construction of a patient table and of an associated medial system.

The example disclosed in the drawings and described hereinafter is to be considered not limited to the specific configuration of the MRI apparatus, but the principles of the inventive teachings are clearly described and the skilled person can use then for any kind of imaging apparatus.

Thus, the table shown in FIGS. 2 to 8 is inspired by the teaching of the present application but not limited to the specific solution used.

FIGS. 2 to 8 show a patient support device configured as a patient support table in which the structure of the table itself is not provided with coil securing receptacles directly on the patient support table. The person skilled in the art would at once appreciate the solution disclosed in the figures and its advantages.

According to the figures a patient support table comprises a patient support plate 107 which is of a rigid material.

The patient support plate has a shape with a cross section, i.e. a section plane perpendicular to the longitudinal axis of the table and perpendicular to the surface of the said support plate, which is shaped like a channel.

A central patient support plate 207 is provided along each longitudinal edge with lateral longitudinal walls 307 extending for the entire length of the plate 207.

The lateral walls 307 forms steps having a substantially vertical extension and these vertical extensions forms abutments for the head ends 117 of the cushions 17 and of cushions having the function of coils securing plates 17'.

Figure 1:
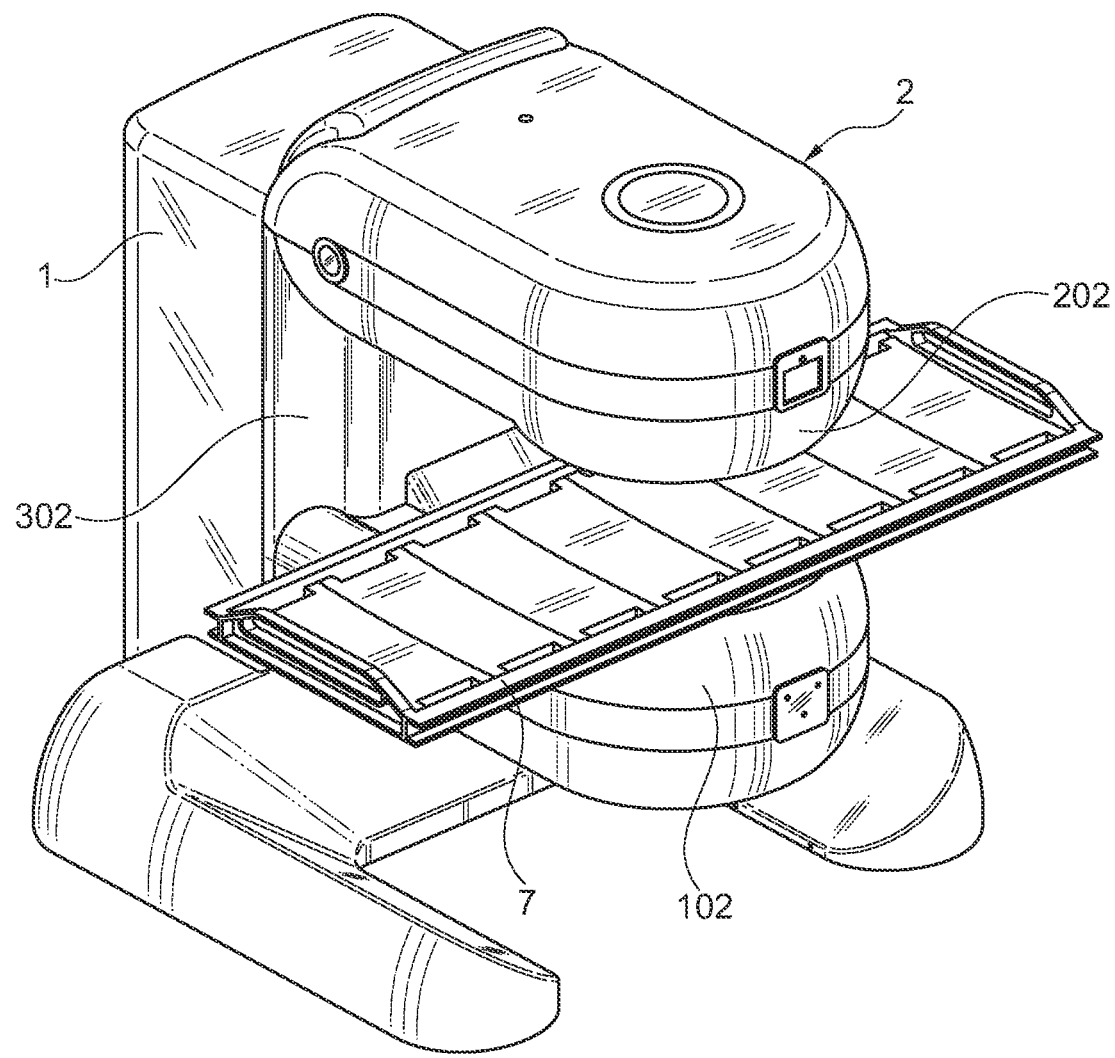
FIG. 1 is a perspective view of a preferred embodiment of a Magnetic Resonance Imaging apparatus, equipped with a patient support device according to the state of the art.
Figure 2:
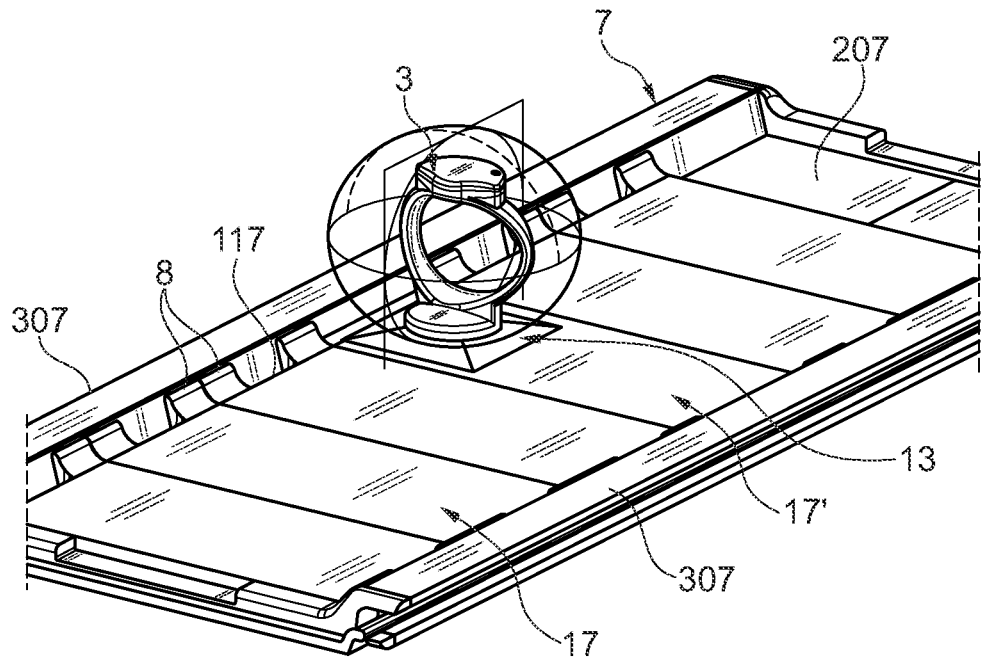
FIGS. 2 and 3 are perspective views of a patient support device according to the present invention and which can be combined with the structure of the MRI apparatus according to FIG. 1.
Figure 3:
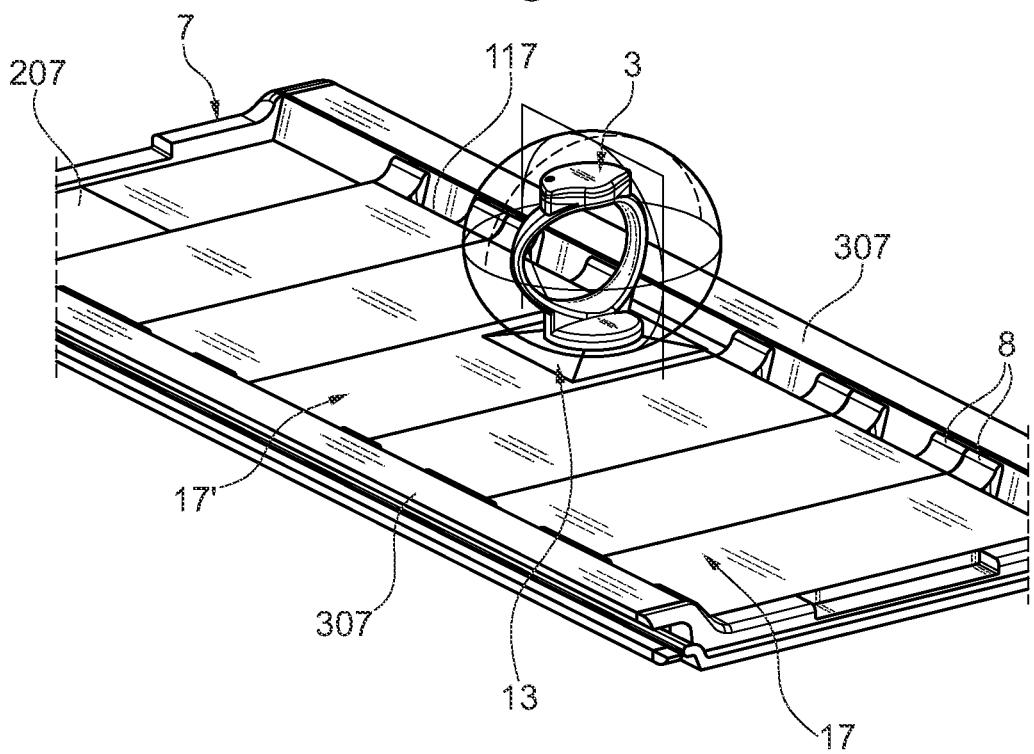
Figure 4:
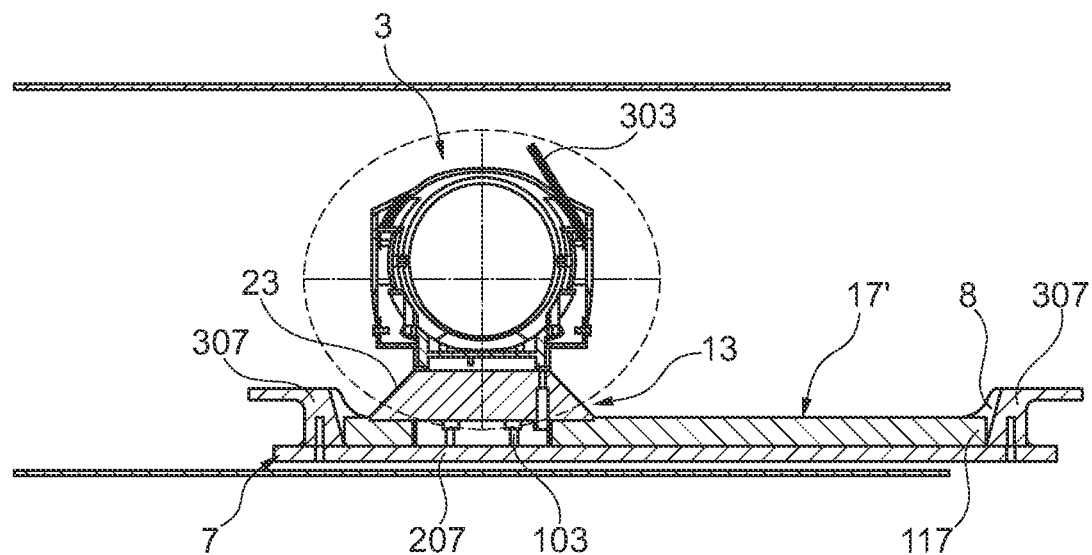
FIG. 4 shows a cross section along a plane which is vertical and perpendicular to the longitudinal axis of the patient support sable or surface.

According to an embodiment which is shown in FIGS. 2, 3 and 4, the cushions 17, 17' do not abut directly against the lateral walls 307, but spacers 8 are provided between each head end of the cushions 17, 17' and the said lateral walls 307.

According to an embodiment, the spacers do not extend for the entire length of the head ends of the cushions 17, 17', but the said spacers are provided only at each corner regions of the said head ends.

According to still a further feature which may be or not be provided in combination with the previous ones the said lateral walls protrude over the surface of the central plate 207 in such a measure that they still protrude over the upper surface of the cushions.

As it appears from the FIGS. 2 and 3 the cushions have everyone an identical extension in the longitudinal direction of the patient support device.

The said cushions have an extension in the direction transverse to the longitudinal axis of the patient support table such that each cushion reaches from one vertical wall to the opposite, fitting precisely between the two abutments formed by the said vertical walls.

At least one of the cushions 17' has the function of a coil 3 securing plate and this cushion 17' is provided with a receptacle 12 in which an engagement element 103 of the coil socket 13 is destined to be releasably secured.

Different kinds of engagement are possible which are within the obvious alternatives known to the skilled person. One way of securing the said socket to the receptacle is press fitting. Another solution may provide for releasable locking means such as the one disclosed in document EP1732438.

As it appears from the embodiment of FIGS. 2 to 8, the socket 13 of the coils 3 has an enlarged base 23 which base has a contact abutting against the surface of the cushion 17' surrounding the receptacle 12.

This enlarged base operates as a stabilizer of the coil socket. Indeed, the large contact surface between socket and cushion distributes the forces acting on the coil 3 on a large surface reducing the local pressure and allowing the coil to have a more stable position.

In the embodiments of the coil 3 illustrated in the FIGS. 2 to 8, the socket 13 and the enlarged base have a pyramidal form with a square base. The square base is centered coaxially with a lower engagement element 103.

Furthermore, according to an embodiment. In order to have a more smooth transition between surface of the cushion 17' and coil socket, the enlarged base is housed within a recessed zone of the cushion 17', the said recessed zone having a shape and dimension corresponding to the one of the enlarged base and furthermore is coaxial to the axis of the receptacle 12.

The said recessed zone 217 also provides for strengthening the coupling between socket 13 and cushion 17' thus increasing the stability of the coil position at the cushion 17'.

Figure 5:
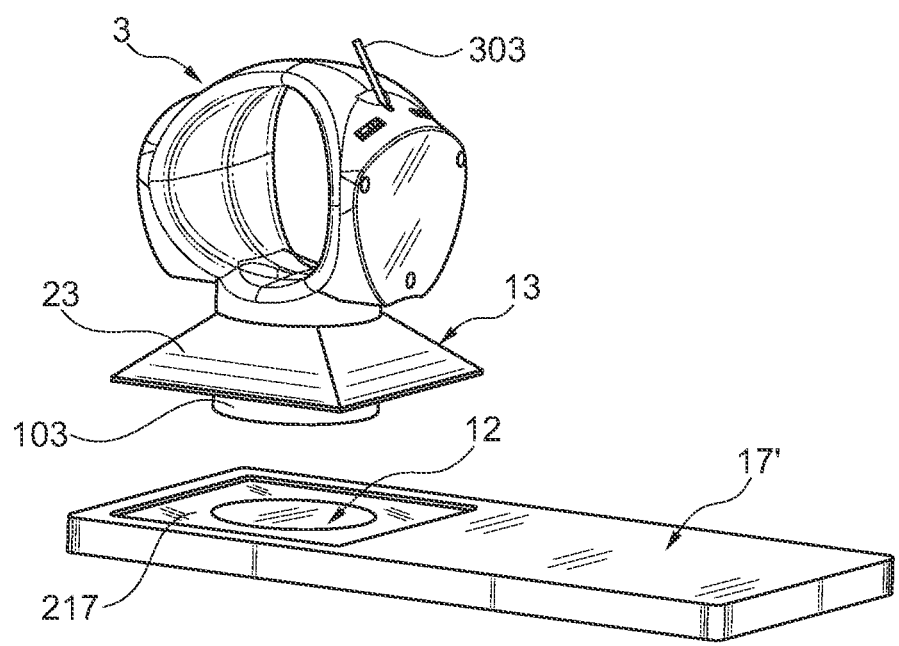
FIG. 5 shows separated from the support surface a coil positioning cushion and a corresponding coil in a perspective exploded view.
Figure 6:
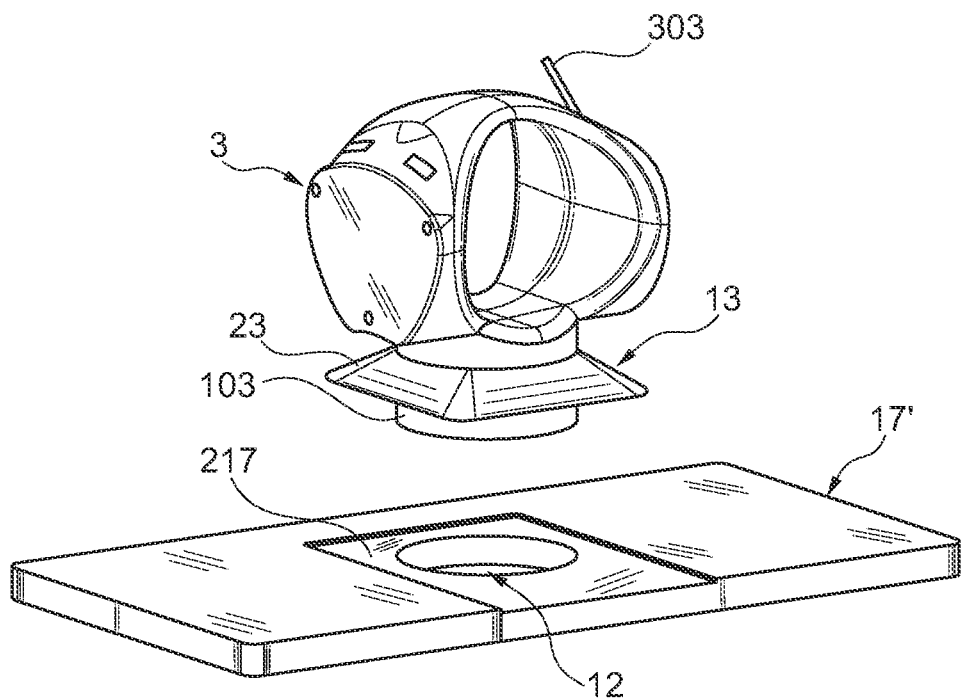
FIG. 6 is a perspective view of a different coil.

As it is shown in FIGS. 4 and 5 the receptacle for securing the coil may be eccentric with respect of the cushion shape, in an alternative embodiment, as shown in FIGS. 6, 7 and 8 the said receptacle 12 is centered on the said cushion 17'.

In combination with a patient support table a set of cushions may comprise at least one cushion 17' according to FIGS. 2 to 4 and at least one cushion 17' according to FIGS. 6 to 8.

The embodiments of FIGS. 2 to 8 show different kind of coils 3. FIGS. 2 to 5 show a closed cylindrical coil.

FIG. 7 show another kind of closed annular coil, while FIG. 8 shows an open coil.

The signals received by the receiving coil 3 is transmitted to the processing unit which generates the image data from the received signals by a cable 303 of which only the initial part at the coil 3 is shown. This connection cable is external to the patient support device and/or to the cushion/s. The end of the cable opposite to the one connecting to the coil 3 and which end is not illustrated is provided with a plug having contact for each of the one or more conductors which may be provided in the cable depending on the kind of receiving coil. The plug is destined to cooperate with a socket comprising corresponding contact terminals to which one or more conductors forming the transmission line to the processing unit of the MRI apparatus are connected (not shown in detail). The socket is mounted on the case of the MRI apparatus, preferably in a position near the patient support table and preferably on a stationary part of the case. Thus no electric line nor any kind of associated connection terminal such as plugs, sockets or the like need to be provided on or inside the patient support and/or the cushion/s. This is advantageous since the patient support device being mounted in a displaceable way relatively to the MRI apparatus, i.e. the magnet structure, it is possible to completely avoid travelling contacts between the electric lines on or in the patient support device and/or the cushion/s and the electric lines provided in or on the case of the stationary part of the MRI apparatus. Such kind of contacts are highly exposed to damaging or to deteriorating their electrical conductivity and thus the quality of the transmitted signal coming from the coil.

Relating to the dimensions of the cushions 17 and 17' in order to be able to place one or more cushions 17' bearing a coil 3 at the correct positions relatively to the body of a person being subjected to an imaging scan, according to one embodiment, a mean body size is selected and the position of the anatomic districts to be imaged is identified. The sizes of the cushions in direction of the longitudinal axis of the support device is calculates as a function of the mutual distance of the said anatomic districts one form the other.

In one variant embodiment at least one cushion may not have an extension in the longitudinal direction of the patient support identical to all the other cushions, so that there might be the possibility of positioning a cushion 17' without the need to observe the step defined by the dimensions of the cushions in the longitudinal direction.

In order to be able to overcome drawbacks which might depend on the very different sizes of the possible patients in relation to body type and/or age, according to a further embodiment, which can be provided in combination with any one of the previous described embodiments, different standard reference sizes of the body to be imaged are selected and a set of cushions 17, 17' may be provided for each of the said selected body sizes.

According to a further variant the definition of each body size is carried out by means of considering the age of the person subjected to imaging.

Thus, each of the said patient support devices may be equipped with at least three different set of cushions 17, 17'.

As it appears clearly from the present description, the specific design of the cushions allows to optimize the number of differently shaped cushions for generating different sets of cushions for the same patient support device according to the real body size of a patient.

Still according to a further variant embodiment, there might be at least one cushion 17, 17', which is formed by two separated halves. The two parts may be cut along a line which is a central line in order to have two half cushions or along a cut which is eccentric.

According to an embodiment, each one of the said cushions is physically separated from the other cushions and the position of all or of at least some of the said cushions relatively to the length of the patient support surface can be exchanged among the said at least some cushions so that all or at least some of the said cushions can occupy different alternative positions relatively to the length of the said patient support surface, thereby changing the position of the receptacle for housing or removably coupling a coil provided on a corresponding cushion relatively to the length of the said patient support table and to the anatomy of the patient.

Referring to the examples shown in FIGS. 2 to 8, the cushion 17' provided with the receptacle 12 can exchange it position with one of the other cushions 17 on its left or right side, so that the coil 3 can be shifted in tralsation steps corresponding about the extension of the cushion in the longitudinal direction of the patient support surface 7. This can be also done with the cushion 17' according to FIGS. 6 to 8.

When the two kinds of cushions 17' provided with a receptacle 12 for a coil 3 are provided at the same time with the other cushions 17 then the position of the two cushions 17' provided with the receptacle 12 can be varied for both the said two cushions 17'.

As it appears clearly by providing different cushions having different extensions in the direction parallel to the longitudinal axis of the patient support table 7, as disclosed above, then the position of the one or two or more cushions 17' provided with the receptacle 12 can be varied along the length of the said patient support table for steps also different of one unitary extension in the longitudinal direction of the patient table.

In combination with one or more of the above disclosed variant embodiments it appears also to be sinergically advantageous to provide different sets of cushions 17, 17' having different extensions in the longitudinal direction of the patient support table such as to allow a combination of these cushions so that a more wide possibility of setting different alternative positions of a cushion 17, 17' along the length of the patient table is made possible and which further may have different kind or positions of receptacles 12.

The invention claimed is:

1. A patient support device, such as a patient bed, table or chair, for use with a Magnetic Resonance Imaging apparatus, wherein said device comprises a patient support surface having such a size as to accommodate at least a part of the patient body, the said device comprising at least one receptacle for housing or removably coupling a coil adapted to receive signals from anatomic regions upon excitation thereof by the Magnetic Resonance Imaging apparatus, which at least one receptacle is arranged in an area of the patient supporting surface corresponding to the position of the anatomic region to be imaged, the patient support surface being covered at least partially by one or more cushions covering in combination the entire patient supporting surface, or at least a part of it, wherein at least one of the said receptacles for coupling to a receiving coil being provided on at least one or more than one of the cushions, the coil once coupled to a corresponding receptacle is connected to a control and processing unit of the MRI apparatus by means of a cable which is external to the said patient support device, and each one of the said cushions is a separate cushion from the other cushions, and independently movable with respect to the other cushions, and the position of all or of at least some of the cushions relatively to the length of the patient support surface can be exchanged among the at least some cushions so that all or at least some of the cushions can occupy different alternative positions relatively to the length of the patient support surface, thereby changing the position of the receptacle for housing or removably coupling a coil provided on a corresponding cushion relatively to the length of the patient support table and to the anatomy of the patient.

2. Patient support device according to claim 1, in which at least part of the cushions have an extension in the direction perpendicular to the longitudinal axis of the support device, which extension corresponding essentially to the width of the patient support surface.

3. Patient support device according to claim 1, in which the cushions have an extension in the longitudinal direction of the patient support device and the said cushions being provided in such a number that the sum of the extensions of the number of cushions provided is essentially equal to the longitudinal extension of the patient support surface.

4. Patient support device according to claim 1, in which the extension of the cushions in the direction parallel to the longitudinal axis of the patient support surface is selected such that the corresponding receptacle for coupling a receiving coil is essentially in a position corresponding to an anatomical district which is diagnostically interesting for being examined by MRI imaging when a patient is positioned on the patient support device.

5. Patient support device according to claim 1, in which the extension of the cushions in the direction parallel to the longitudinal axis of the patient support surface is calculated as a function of the average dimensions of the anatomical structure of a normal adult person or of a child.

6. Patient support device according to claim 1, in which the at least one receptacle for housing or removably coupling a coil is provided in a dedicated coil securing plate which is a coil specifically designed cushion or element substituting at least one cushion.

7. Patient support device according to claim 1, in which the extension of the cushions in the direction parallel to the longitudinal axis of the patient support surface is identical for each cushion or coil securing plate.

8. Patient support device according to claim 1, wherein the support device comprises a patient support table which is mounted in a slidable way along at least one direction or additionally along at least one further different direction on a base associated to the gantry of an MRI apparatus.

9. Patient support device according to claim 1, wherein the support device comprising a patient table having a containment wall along at least one of its peripheral edges against which the corresponding peripheral edge of the cushion or of the coil securing plate abuts.

10. Patient support device according to claim 9, in which the containment wall is provided along at least the two longitudinal edges of the table, the cushions and the coil securing plate having an extension in the direction perpendicular to the longitudinal edges corresponding essentially to the distance of the facing sides of the two containment walls each head end of the cushions abutting against the corresponding containment wall.

11. Patient support device according to claim 1, in which the receptacle for housing/coupling the receiver coil includes means for removable mechanical connection of the receiver coil.

12. Patient support device according to claim 1, in which the coil comprises a lower extension engageable in the receptacle, the extension projecting out form the enlarged lower face of a foot of the coil destined to abut against the surface of the cushion or of the coil securing plate surrounding the receptacle.

13. Patient support device according to claim 1, in which each of the coils is provided with a securing foot engaging by press fitting in a corresponding receptacle of a cushion or of a coil securing plate.

14. Patient support device according to claim 1, the support device being provided in combination with at least one NMR signal receiving coil, the coil being provided with a socket configured to engage a corresponding receptacle, the set of cushions dimensioned such that the set of cushions covers, when positioned on the patient support surface, the entire extension of the surface;

the set of cushions comprising at least one first cushion provided with a coil securing receptacle configured to releasable engage the securing socket of a receiving coil;

at least a further cushion having a coil securing receptacle which is modified relatively to the first cushion in relation to the position of the receptacle along the cushion surface or in relation to the design or configuration of the receptacle for being in conformity with a further different socket;

at least a further cushion not showing any receptacle but having different dimensions, particularly a different extension in at least one direction particularly in a direction parallel to the longitudinal axis of the patient support device.

15. Patient support device according to claim 1, in which two or more of the cushions are provided in a set, each set comprising at least one cushion with a coil securing receptacle, at least one cushion without any receptacle, the sets of cushions having dimensions in the direction of the longitudinal axis of the patient support device which are determined as a function of the height of samples of patient body having different heights.

16. Patient support device according to claim 15, in which the samples of patient body are selected among the ones in the following list: baby, adolescent, adult, small, medium and tall adult.

17. Patient support device according to claim 1, wherein the at least one receptacle is for housing and removably coupling a coil adapted to receive signals from anatomic regions upon excitation thereof by the Magnetic Resonance Imaging apparatus.

* * * * *